(12) United States Patent
Bakker et al.

(10) Patent No.: US 6,423,013 B1
(45) Date of Patent: Jul. 23, 2002

(54) SYSTEM AND METHOD FOR ASSESSING BREATHING AND VOCAL TRACT SOUND PRODUCTION OF A USER

(75) Inventors: Klaas Bakker; Richard N. Biagioni; Mary R. Byrne; Thomas A. Byrne; Ronald W. Netsell, all of Springfield, MO (US)

(73) Assignee: The Board of Governors of Southwest Missouri State University, Springfield, MO (US)

( * ) Notice: Subject to any disclaimer, the term of this patent is extended or adjusted under 35 U.S.C. 154(b) by 0 days.

(21) Appl. No.: 09/662,048

(22) Filed: Sep. 15, 2000

(51) Int. Cl.$^7$ ................................................ A61B 7/00
(52) U.S. Cl. ...................................... 600/586; 600/529
(58) Field of Search ............................ 600/23, 21, 529, 600/530, 531, 532, 533, 534, 535, 536, 537, 538, 539, 540, 541, 542, 543, 586–595

(56) References Cited

U.S. PATENT DOCUMENTS

| | | | |
|---|---|---|---|
| 4,036,217 A | | 7/1977 | Ito et al. |
| 4,270,547 A | | 6/1981 | Steffen et al. |
| 4,296,757 A | * | 10/1981 | Taylor ........................ 600/534 |
| 4,422,458 A | | 12/1983 | Kravath |
| 4,732,159 A | | 3/1988 | Kraman |
| 5,735,268 A | | 4/1998 | Chua et al. |
| 5,765,135 A | | 6/1998 | Friedman et al. |
| 5,794,614 A | | 8/1998 | Gruenke et al. |
| 5,808,540 A | | 9/1998 | Wheeler et al. |
| 5,865,168 A | | 2/1999 | Isaza |
| 5,868,677 A | | 2/1999 | Iwanaga et al. |
| 6,261,238 B1 | * | 7/2001 | Gavriely ...................... 600/532 |

OTHER PUBLICATIONS

Godfrey E. Arnold, M.D., Spastic Dysphonia: Changing Interpretations of a Persistant Affliction, Logos, vol. 2, No. 1, Apr. 1959, 12 pages.

(List continued on next page.)

*Primary Examiner*—Kevin Shaver
*Assistant Examiner*—Pamela L. Wingood
(74) *Attorney, Agent, or Firm*—Senniger, Powers, Leavitt & Roedel (57) ABSTRACT

A system and method for assessing breathing and vocal tract sound production of a user. The system comprises a first sensor generating a vocal tract sound signal representing vocal tract sounds produced by the user, a second sensor generating a breathing signal representing breathing movement of the user, and a signal processing unit for processing the vocal tract sound and breathing signals. The method comprises the steps of sensing vocal tract sounds produced by the user and providing a vocal tract sound signal representative thereof, sensing breathing movement of the user and providing a breathing signal representative thereof, receiving the signals via an analog input for processing the signals, generating a combined signal by superimposing the vocal tract sound and breathing signals, and displaying the combined signal to the user.

21 Claims, 7 Drawing Sheets

OTHER PUBLICATIONS

Goebel, Hillis, and Meyer, The Relationship Between Speech Fluency and Certain Patterns of Speechflow, Presented as a technical paper—ASHA, 1985, 8 pages.

Murdoch, Chenery, Bowler, and Ingram, Respiratory Function in Parkinson's Subjects Exhibiting A Perceptible Speech Deficit; A Kinematic And Spirometric Analysis, Journal of Speech and Hearing Disorders, vol. 54, Nov. 1989, pp. 610–626.

Manifold and Murdoch, Speech Breathing in Young Adults: Effect of Body Type, Journal of Speech and Hearing Research, vol. 36, Aug. 1993, pp. 657–671.

Respitrace website materials dated 1998 accessed Jun. 10, 1999, 3 pages.

Excerpts from Visipitch II training manual, date unknown, 15 pages.

Annandale Fluency Clinic brochure, circa 1985, 2 pages.

Cafet for Kids Turns Worlds into Action Brochure, circa 1985, 8 pages.

Cafet Pricing Brochure, circa 1994, 2 pages.

This is the Technical Reason You'll Want to Switch to Cafet for Treating Stutterers Brochure, circa 1986, 6 pages.

Child Fluency Trainer (CFT) Brochure, date unknown, 1 page.

Goeble, The Use of a Microcomputer in Fluency Therapy, reprinted from the 1986 Computer Conference Proceedings American Speech–Language–Hearing Foundation, Orlando, Florida, circa 1986, 5 pages.

Goebel, C.A.F.E.T. Computer–Aided Fluency Establishment Trainer, An Overview of the Program, circa 1987, 7 pages.

* cited by examiner

SYSTEM AND METHOD FOR ASSESSING BREATHING AND VOCAL TRACT SOUND PRODUCTION OF A USER

BACKGROUND OF THE INVENTION

1. Field of the Invention

The present invention relates to a system and method in the field of speech therapy. In particular, this invention relates to a system and method for assessing breathing and vocal tract sound production of a user. This invention is also applicable to users who are deaf or hearing impaired, users suffering from neurogenic communication disorders, users with voice disorders, and users who stutter. This invention is also applicable in the field of singing instruction.

2. Description of the Prior Art

A range of electronic and non-electronic devices exist for the measurement and feedback of volume changes during breathing. Some non-electronic devices, such as spirometers, have limitations for use during speech production as they require the client to breathe through some type of tubing. Spirometers are primarily useful for measuring the maximum capacity ("vital capacity") or typical capacity ("tidal volume") of one's respiratory function as an indication of one's health and, in some cases, whether or not speech and voicing are possible. However, these systems are not well-suited for the training of good speech breathing habits.

Other systems provide feedback for breathing in general. While these systems are not specifically designed to give feedback on speech breathing, some of the systems can potentially be adjusted to do this by connecting a sound source to an additional signal processing input on the system. However, these systems are expensive and require installation of signal processing hardware preventing convenient connection to portable laptop computers. In addition, the feedback from these systems is not specifically adjusted to the needs of speech language pathologists or trainers of speech to the deaf or hearing impaired. In particular, such feedback does not provide integrated and clinically adjusted feedback of a user's speech breathing habits.

Other systems train different speech breathing habits specifically for the reduction of stuttering. These systems transduce sound and breathing behaviors to provide separate graphical displays of each behavior. These systems comprise either one or two belts for transducing breathing behaviors. These systems also require separate signal processing hardware.

Some systems train people who stutter how to produce gentle voice onsets in speech while also severely slowing down all speech and following one particular treatment approach. These systems include a microphone and one or two breathing sensors connected to a computer. All signals are converted from analog to digital via circuitry external to the computer. However, such systems are not well-suited for disorders other than stuttering or for methodologies other than certain stuttering treatment methodologies. The breathing feedback is not designed to compare volume changes with the absence or presence of speech and with the absence or presence of voicing in speech. Such systems fail to provide comprehensive feedback on speech and breathing.

For these reasons, an improved speech therapy system and method is desired for providing more convenient and effective treatment of users who are deaf or hearing impaired, users suffering from neurogenic communication disorders, users with voice disorders, and users who stutter.

SUMMARY OF THE INVENTION

It is an object of this invention to provide a system useful for the training of good speech breathing habits.

It is an object of this invention to provide a system which is inexpensive and can be connected to portable laptop computers.

It is an object of this invention to provide a system with feedback that is specifically adjusted to the needs of speech language pathologists or trainers of speech to the deaf or hearing impaired.

It is an object of this invention to provide a system which provides integrated and clinically adjusted feedback of a user's speech breathing habits.

It is an object of this invention to provide a system which integrates the sound and breathing signals for convenience to clinicians and clients.

It is an object of this invention to provide a system which includes separate thoracic and abdominal breathing sensors for representing breathing.

It is an object of this invention to provide a system which provides generically useful feedback on speech and breathing, not limited specifically to one user population such as people who stutter.

It is an object of this invention to provide a system which provides breathing feedback designed to compare volume changes with the absence or presence of speech and with the absence or presence of voicing in speech.

It is an object of this invention to provide a system which provides comprehensive feedback on speech and breathing.

In one form, a system for assessing breathing and vocal tract sound production of a user embodies aspects of the invention. The system has a first sensor, a second sensor, and a signal processing unit. The first sensor generates a vocal tract sound signal representing vocal tract sounds produced by the user. The second sensor generates a breathing signal representing breathing movement of the user. The signal processing unit processes the vocal tract sound and breathing signals. The signal processing unit includes an analog input receiving the vocal tract sound and breathing signals from the first and second sensors, respectively, and a processor generating a combined signal displaying a superimposition of the received signals to the user.

In yet another form, the invention is directed to a method for assessing breathing and vocal tract sound production of a user. The method includes the steps of sensing vocal tract sounds produced by the user and providing a vocal tract sound signal representative thereof, sensing breathing movement of the user and providing a breathing signal representative thereof, receiving the signals via an analog input for processing the signals, generating a combined signal by superimposing the vocal tract sound and breathing signals, and displaying the combined signal to the user.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF PREFERRED EMBODIMENTS

Referring to the drawings, the system and method (hereinafter, "the system 100") of the invention assesses breathing and vocal tract sound production of a user 102 or client. Vocal tract sound production includes any sound produced by the human upper respiratory system from the larynx to the mouth and nose of the user 102. Speech sound production is one form of vocal tract sound production which combines phonation in the larynx with articulation. The system 100 can be used as an intervention tool allowing an instructor and/or the user 102 to modify or monitor the user's respiratory patterns during speech production.

The system 100 is generically useful for the treatment and non-clinical training of good speech breathing habits.

The system 100 features sophisticated and comprehensive feedback screens that can be adjusted to age groups or treatment purposes. The system 100 provides feedback in which speech, sound, and speech breathing are preferably integrated in a single feedback display 116. In addition, the system 100 is portable, inexpensive, and user-friendly. Advantageously, system 100 uses a standard laptop computer as its signal processing equipment. The system 100 is designed to be of use to a variety of clients including, but not limited to: speakers who are deaf or hearing impaired, neurologically-impaired speakers, speakers who stutter, and voice patients or students.

Figure 1:
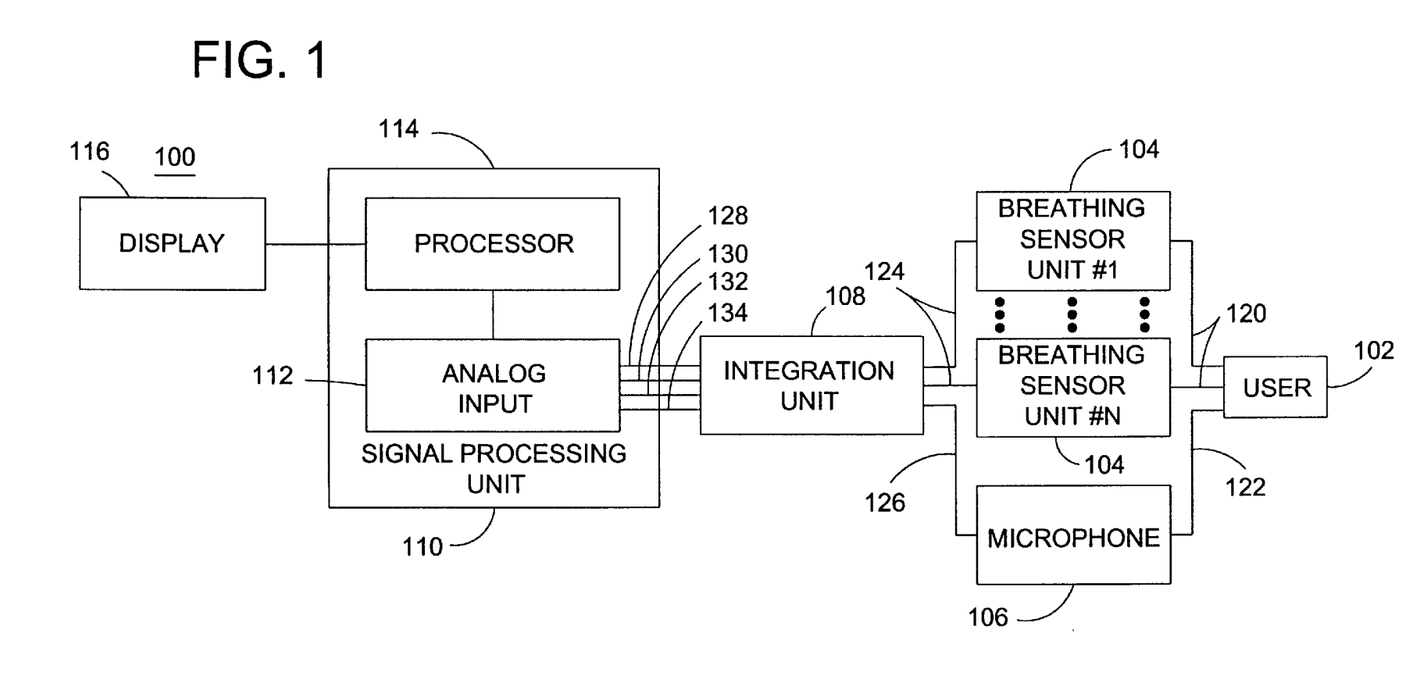
FIG. 1 is a block diagram of a system for assessing breathing and vocal tract sound production according to a preferred embodiment of the invention.

Referring first to FIG. 1, a block diagram of a preferred embodiment of the system 100 of the invention illustrates several main components. The user 102 produces vocal tract sounds indicated at reference character 122 and breathing movements or other breathing motions, indicated at reference character 120, which are converted to analog electrical signals by at least one breathing sensor unit 104, at least one microphone 106, and an integration unit 108. The breathing sensor unit 104, or other resistance device, is attached to a stretchable belt (see FIG. 5D, reference character 526). The belt is positioned around the user's torso. In one embodiment, one breathing sensor unit 104 is positioned adjacent to the upper chest (e.g., midpoint between the clavicular notch and the sternal notch) to measure thoracic breathing movement, while another breathing sensor unit 104 is positioned adjacent to the lower chest (e.g., at the navel) to measure abdominal breathing movement. The breathing sensor units 104 and the microphone 106 are electrically connected in parallel to the integration unit 108. In an alternative embodiment, the breathing sensor units 104 and the microphone 106 are electrically connected in series. By using at least two breathing sensor units 104 positioned as described above, an accurate determination of the breathing movement 120 of the user 102 is achieved. An accurate determination of the breathing movement 120 allows the system 100 to be used not only for the treatment of people who stutter but also for the instruction of voice students and the treatment of people who are deaf or who have neurogenic communication disorders.

The system 100 preferably comprises a first sensor 106, a second sensor 104, and a signal processing unit 110. When the user 102 attempts speech sound production, first there is breathing and then there is vocal tract related sound. The first sensor 106 generates a vocal tract sound signal at line 126 representing vocal tract sounds 122 produced by the user 102. The second sensor 104 generates a breathing signal at line 124 representing breathing movement 120 of the user 102. The signal processing unit 110 processes the vocal tract sound and breathing signals at lines 126, 124 simultaneously. The signal processing unit 110 includes an analog input 112 receiving the vocal tract sound and breathing signals from the first 106 and second 104 sensors, respectively. As will be described below, a processor 114 generates a combined signal which represents a superimposition of the received signals to the user 102. The combined signal is displayed to the user 102 in apparent real-time on display 116.

Figure 6:
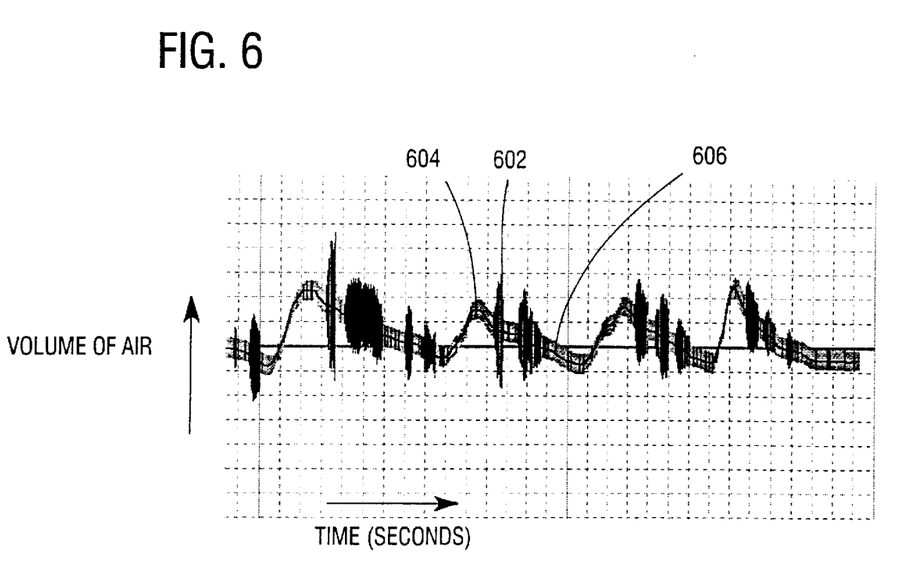
FIG. 6 is a graph illustrating an exemplary vocal tract sound signal superimposed onto an exemplary breathing signal produced by the system of FIG. 1.
Figure 7:
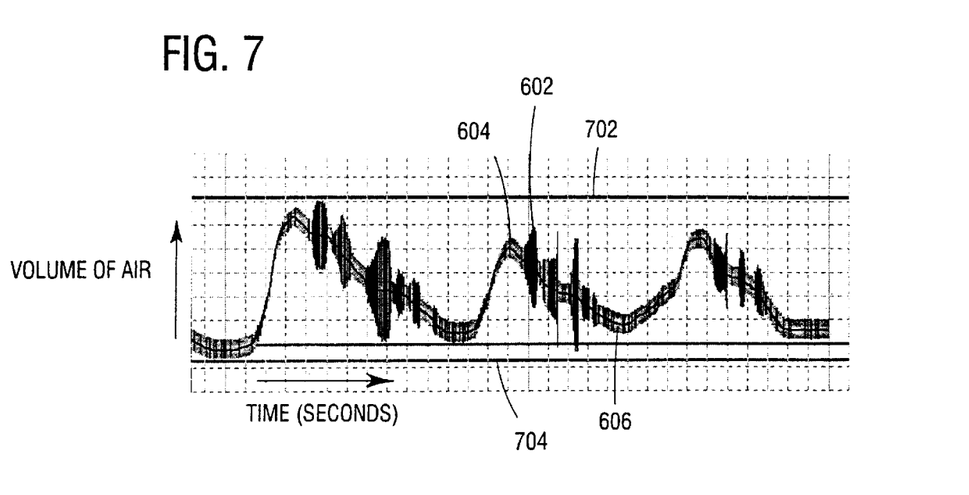
FIG. 7 is a graph illustrating an exemplary vocal tract sound signal superimposed on an exemplary breathing signal produced by the system of FIG. 1 with recommended maximum and minimum breathing levels shown.

In one embodiment, the breathing sensor units 104 convert volumetric displacement representing the user's breathing movements 120 to representative electrical breathing signals (see FIGS. 6 and 7). For example, two breathing sensor units 104 can be positioned adjacent to the abdomen and thorax of the user 102 to generate abdominal and thoracic breathing signals. The integration unit 108 receives and combines the abdominal and thoracic breathing signals for transmission on a single wire or other electrical transmission channel to the signal processing unit 110. The integration unit 108 combines the abdominal and thoracic breathing signals by alternately sampling and outputting either signal as an integrated breathing signal at line 128. The integration unit 108 alternates sampling the abdominal and thoracic breathing signals at a user-defined sampling rate. A measurement cycle reflects the amount of time spent sampling and outputting either the abdominal or thoracic breathing signals as the integrated breathing signal. In a preferred embodiment, software associated with signal processing unit 110 reads the processed vocal tract sound signal and voicing status signal once while reading the integrated breathing signal twice (to obtain both abdominal and thoracic measurements) every $\frac{1}{20}$th of a second. However, the instructor or user 102 adjusts this value depending on the particular user 102.

In addition, the integration unit 108 produces a breathing source signal at line 132 which identifies the integrated breathing signal as either the abdominal or thoracic breathing signal. The integrated breathing signal at line 128 and breathing source signal at line 132 are preferably transmitted by the integration unit 108 to the signal processing unit 110 via the analog input 112. In one embodiment, the integration unit 108 and associated circuitry obtain power from the signal processing unit 110.

Similarly, the microphone 106 transduces the vocal tract sounds 122 produced by the user 102 into the vocal tract sound signal at line 126 for transmission to the integration unit 108. The integration unit 108 processes the vocal tract sound signal 126 via a volume circuit 200 (see FIG. 2) and a voicing detection 300 circuit (see FIG. 3). After processing, integration unit 108 transmits the processed vocal tract sound signal 130 to the signal processing unit 110 via the analog input 112. In addition, the integration unit 108 transmits a voicing status signal 134 to the signal processing unit 110 to indicate the presence or absence of voicing.

The abdominal breathing, thoracic breathing, integrated breathing, breathing source, vocal tract sound, processed vocal tract sound, and voicing status signals are analog signals received by the signal processing unit 110.

The signal processing unit 110 or other processing device comprises the processor 114 and the analog input 112. The processor 114 causes display 116 to show recommended minimum and maximum breathing volume levels to the user 102. These levels are represented by horizontal lines on the display 116. In a preferred embodiment, processor 114 also causes display 116 to display the proper phrasing of speech as a function of time. This phrasing is represented by vertical lines on display 116. The analog input 112 receives the analog integrated breathing and processed vocal tract sound signals via lines 128 and 130 respectively. Because all signals received by the signal processing unit 110 are in analog form via the analog input 112, the signal processing unit 110 contains an analog-to-digital (A/D) converter. In one embodiment, the signal processing unit 110 is a laptop computer, the analog input 112 is at least one joystick input typically associated with a sound card in the laptop computer, and display 116 is a monitor associated with the laptop computer. The A/D converter is located within the joystick input section of the sound card, eliminating the extra cost and extra space needed for a separate circuit board to perform A/D conversions. In addition, laptop computers are affordable and portable making the system 100 applicable to instructors in applied settings such as public schools.

Processing the received signals includes combining the integrated breathing and processed vocal tract sound signals by superimposing the signals on the display 116 for view by the user 102. Processing also includes converting the integrated breathing and processed vocal tract sound signals into digital format.

In one embodiment, the functionality of the integration unit 108 and associated circuitry is performed digitally within the signal processing unit 110.

In one embodiment, the microphone 106 is connected to the breathing sensor unit 104. The abdominal and thoracic breathing signals as well as the vocal tract sound signal are transmitted to the integration unit 108 via a single electrical wire harness.

In another embodiment, the signal processing unit 110 includes a speaker or headphone output (not shown) for reproducing the vocal tract sounds 122 to the user 102 or instructor.

Figure 2:
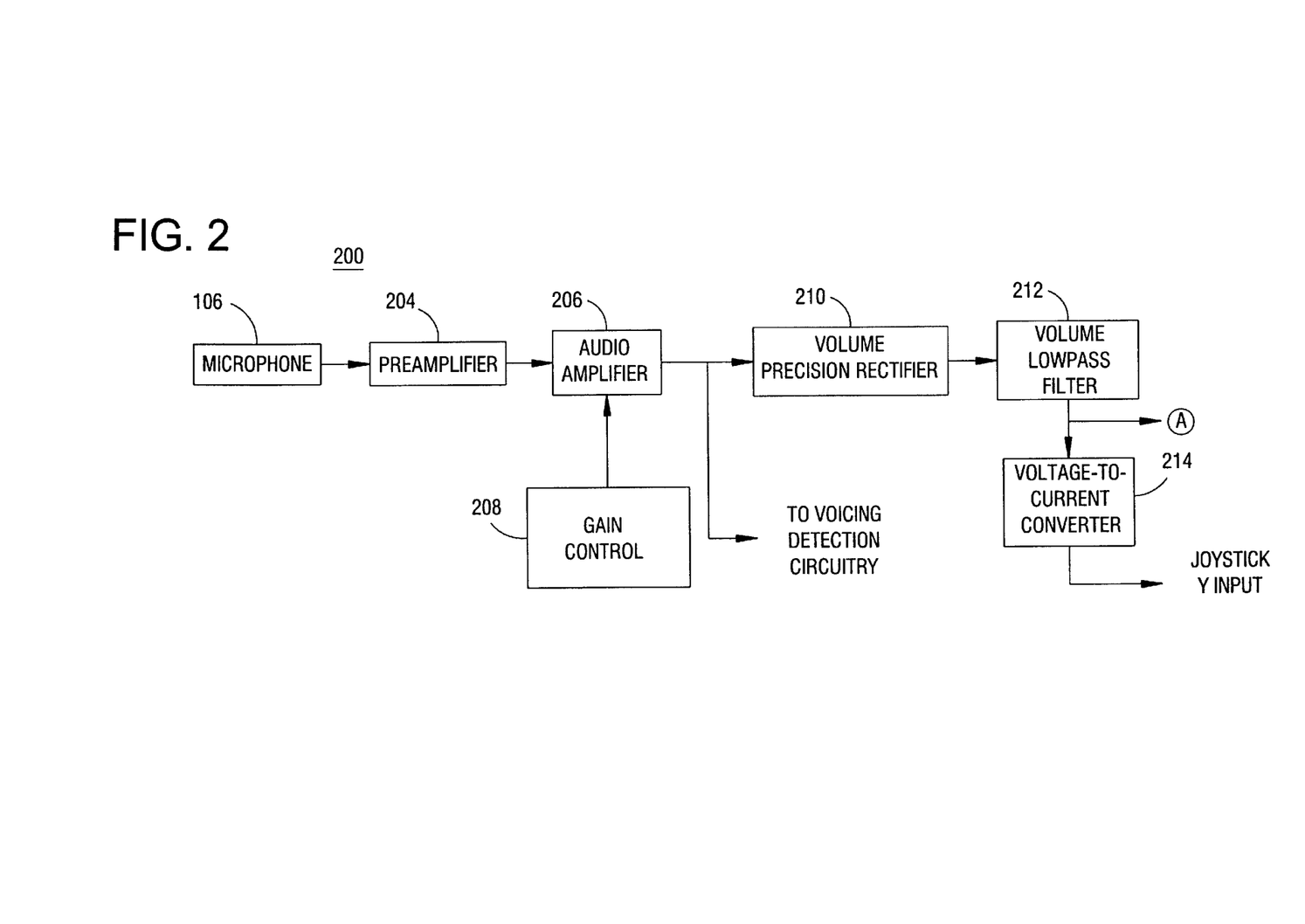
FIG. 2 is a block diagram of volume circuitry of the system of FIG. 1.

Referring next to FIG. 2, a block diagram of a preferred embodiment of the system 100 illustrates the volume circuitry 200. In one embodiment, integration unit 108 contains the volume circuitry 200. Volume circuitry 200 amplifies a raw signal from microphone 106, measures its amplitude, and provides the processed vocal tract sound signal proportional to an input sound level produced by the user 102. The processed vocal tract sound signal output is adjustable via a potentiometer. The transduced sounds from the microphone 106 pass through a preamplifier 204, an audio amplifier 206, a volume precision rectifier 210, a volume lowpass filter 212, and a voltage-to-current converter 214 before transmission as the processed vocal tract sound signal at line 130 to the signal processing unit 110 via the analog input 112. The processed vocal tract sound signal is an analog current signal. Standard joystick input sections of sound cards have an X input, a Y input, and a first and second pushbutton inputs. In one embodiment where the analog input 112 is a joystick input, the processed vocal tract sound signal connects to the Y input of the joystick input. Standard joystick circuitry assumes resistance inputs. When the joystick circuitry reads the processed vocal tract sound signal, a high current reading is interpreted as a low resistance reading and vice-versa. The conversion effectively produces an inverse reading, with volume proportional to the inverse of the resistance reading. The inverse relationship is corrected by the processor 114 in software.

Figure 3:
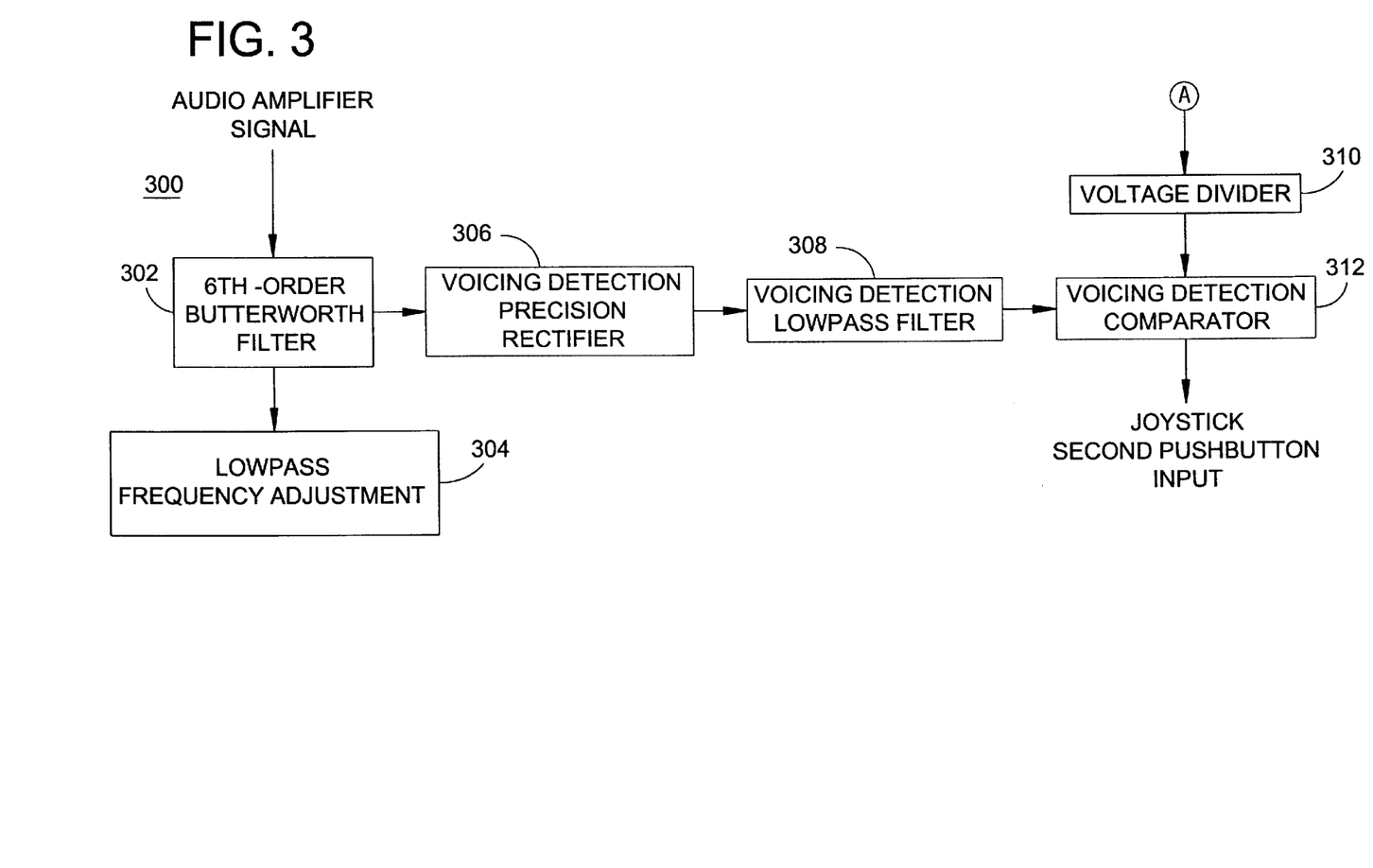
FIG. 3 is a block diagram of voicing detection circuitry of the system of FIG. 1.

The volume precision rectifier 210, volume lowpass filter 212, and voltage-to-current converter 214 comprise an amplitude measurement circuit. The outputs of the audio amplifier 206 and the volume lowpass filter 212 also connect to the voicing detection circuitry 300.

A gain control 208 connects to the audio amplifier 206. The gain control 208 adjusts the gain of the vocal tract sound signal at line 126 being processed. In one embodiment, gain control 208 is a potentiometer mounted on integration unit 108.

In one embodiment, the preamplifier 204 is a 741 operational amplifier and the audio amplifier 206 is a 386 operational amplifier. Those skilled in the art will note that simpler circuits, such as those based on a single 386 operational amplifier, will produce similar results. The volume precision rectifier 210 circuit is preferably based on a 741 operational amplifier and the volume lowpass filter 212 is a resistance-capacitor filter with a time constant of approximately 100 milliseconds.

The voltage-to-current converter 214 adds a small offset voltage to the vocal tract sound signal so that the voltage input to the converter 214 never drops to zero. A nominal algorithm for conversion is one volt to one milliampere. Those skilled in the art will note that details of such converter 214 circuits are commonly known in the field.

Referring next to FIG. 3, a block diagram of a preferred embodiment of the system 100 of the invention illustrates voicing detection circuitry 300. Voicing detection circuitry 300 distinguishes between the presence of voicing (or voiced speech) and the absence of voicing (or voiceless speech) in the amplified vocal tract sound signal providing an indication of voice onset (see FIG. 6, reference character 602) by the user 102 during a respiratory cycle. The respiratory cycle is composed of one inhalation and exhalation by the user 102. The voicing detection circuitry 300 distinguishes between those sounds originating from larynx vibrations and those sounds produced by passing air through the vocal tract or those sounds which are background noise. In one embodiment, the voicing detection circuitry 300 is contained within the integration unit 108. The voicing detection circuitry 300 is intended to determine whether or not the user 102 is creating "voiced" sounds that include a fundamental frequency of phonation. The signal from the audio amplifier 206 connects to a 6th-order Butterworth filter 302, a voicing detection precision rectifier 306, a voicing detection lowpass filter 308, and a voicing detection comparator 312 before transmission as the voicing status signal 134 to the signal processing unit 110 via the analog input 112. In one embodiment where the analog input 112 is a joystick input, the voicing status signal 134 connects to the second pushbutton input of the joystick input. The signal from the volume lowpass filter 212 also connects to a voltage divider 310 before connecting to the comparator.

In one embodiment, the Butterworth filter 302 is an integrated circuit component with a lowpass frequency adjustment 304 via a potentiometer from 80 to 600 cycles per second (Hz). Such a lowpass frequency range accommodates fundamental frequencies anticipated for most users 102 from adult males with deep voices to young children with high-pitched voices. The Butterworth filter 302 automatically adjusts its offset so that the filtered signal is centered at zero volts.

In one embodiment, the voicing detection lowpass filter 308 has a time constant of approximately 100 milliseconds.

The voltage divider 310 attenuates the signal from the audio amplifier 206 and connects to the voicing detection comparator 312. The voltage divider 310 is adjustable at the circuit board level, but not by the user 102.

The voicing detection comparator 312 changes state depending on whether or not the signal from the voicing detection lowpass filter 308 is greater than or less than the attenuated signal from the voltage divider 310. In one embodiment, the voicing detection comparator 312 employs an open collector output compatible with transistor-transistor logic (TTL). A comparator outputs either a HI or LO signal. An output of HI indicates that voicing is not occurring while an output of LO indicates that voicing is occurring.

Figure 4:
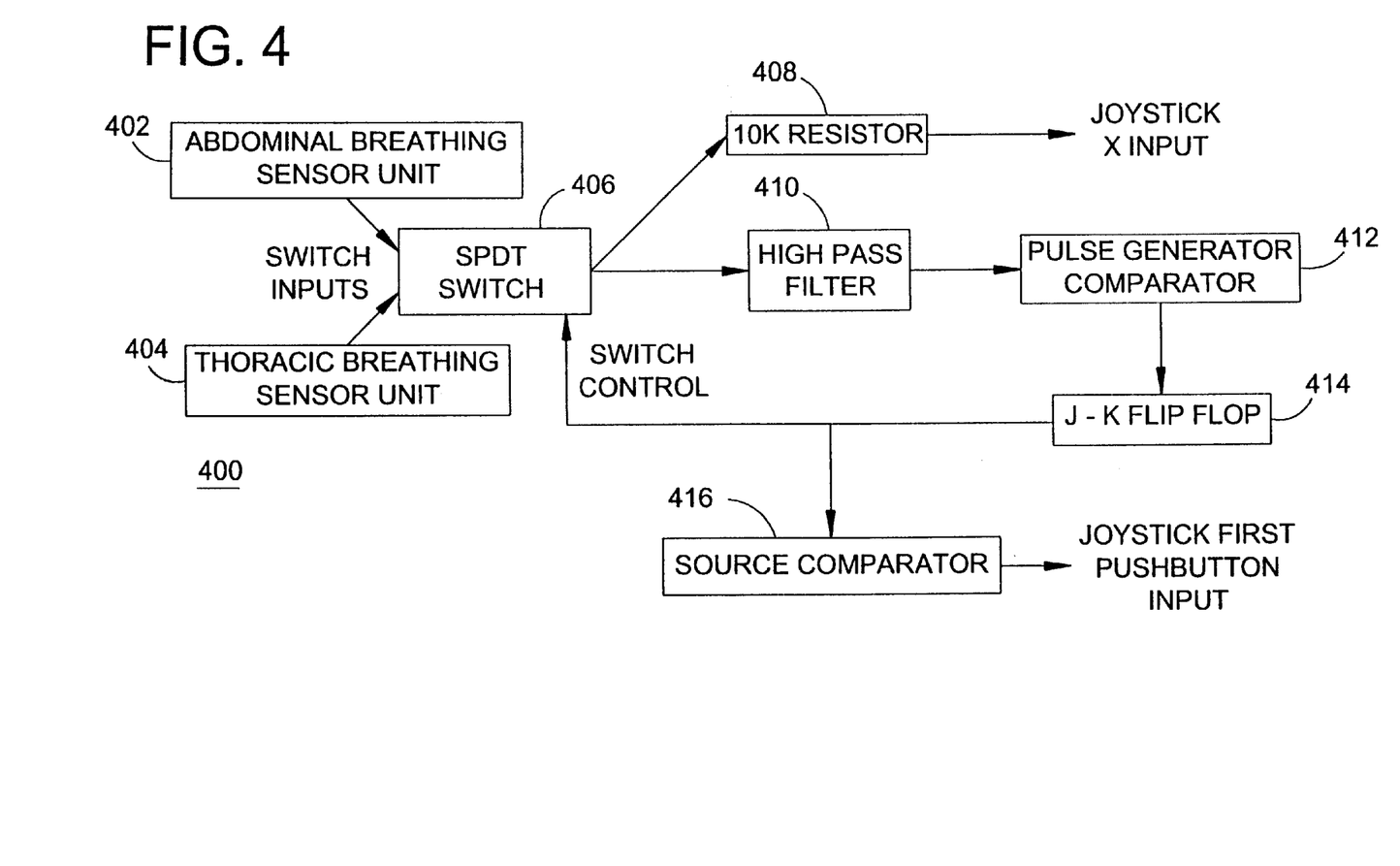
FIG. 4 is a block diagram of breathing measurement circuitry of the system of FIG. 1.

Referring next to FIG. 4, a block diagram of a preferred embodiment of the system 100 of the invention illustrates breathing measurement circuitry 400. In the illustrated embodiment, integration unit 108 contains the breathing measurement circuitry 400. The breathing measurement circuitry 400 is designed to allow the abdominal and thoracic breathing signals from two breathing sensor units 402, 404 (used to measure abdominal and thoracic breathing respectively) to be sampled in alternate measurement steps. A sharp drop in potential occurs as a consequence of an internal reset of circuitry associated with the analog input. Control of which breathing sensor unit 402, 404 is being read is based on this sharp drop in potential upon completion of the measurement cycle. The sharp drop is used to toggle a J-K flip-flop 414 circuit which in turn controls a single-pole double throw (SPDT) switch 406 and a source comparator 416. The SPDT switch 406 selects either the abdominal breathing sensor unit 402 or the thoracic breathing sensor unit 404. In one embodiment, the SPDT switch 406 is an integrated circuit component and the breathing sensor units 402, 404 are linear slide potentiometers.

The abdominal 402 and thoracic 404 breathing sensor units produce abdominal and thoracic breathing signals, respectively. These signals pass through the SPDT switch 406 and a ten kilo-ohm resistor 408 before transmission as the integrated breathing signal 128 to the signal processing unit 110 via the analog input 112. In one embodiment where the analog input 112 is a joystick input, the integrated breathing signal 128 connects to the X input of the joystick input.

The SPDT switch 406 also connects to a highpass filter 410, a pulse generator comparator 412, and J-K flip-flop 414. The output from J-K flip-flop 414 controls the SPDT switch 406. The output from J-K flip-flop 414 also controls source comparator 416 providing the breathing source signal 132 for transmission to the signal processing unit 110 via the analog input 112. In one embodiment where the analog input 112 is a joystick input, the breathing source signal 132 connects to a first pushbutton input of the joystick input. The pulse generator comparator 412 is designed with hysteresis such that a sudden drop in the input potential causes its output to change states for a few milliseconds, producing a TTL pulse. This occurs at the end of each measurement cycle.

The operation of the breathing measurement circuitry 400 is as follows. The software stores the analog value at the X input into data arrays representing either abdominal or thoracic measurements based on the status of the first pushbutton. Initially, the first pushbutton of the joystick input reads logic HI and SPDT switch 406 is selecting the abdominal breathing sensor unit 402. A software command instructs the joystick input to read the first pushbutton and X inputs, so measurement of abdominal breathing sensor unit 402 is accomplished. At the end of the measurement cycle, the breathing measurement circuitry 400 sets the logic of the first pushbutton to LO and toggles SPDT switch 406 to select thoracic breathing sensor unit 404. In the next software-controlled measuring cycle, the software simultaneously reads the values of the first pushbutton and the analog value at the X input. Recognizing that the value of first pushbutton changed to LO, the software stores the analog value at the X input into a data array for thoracic measurements. The process continues in this fashion with SPDT switch 406 alternating sampling between abdominal 402 and thoracic 404 breathing sensor units.

Figures 5A, 5B, 5C, 5D:
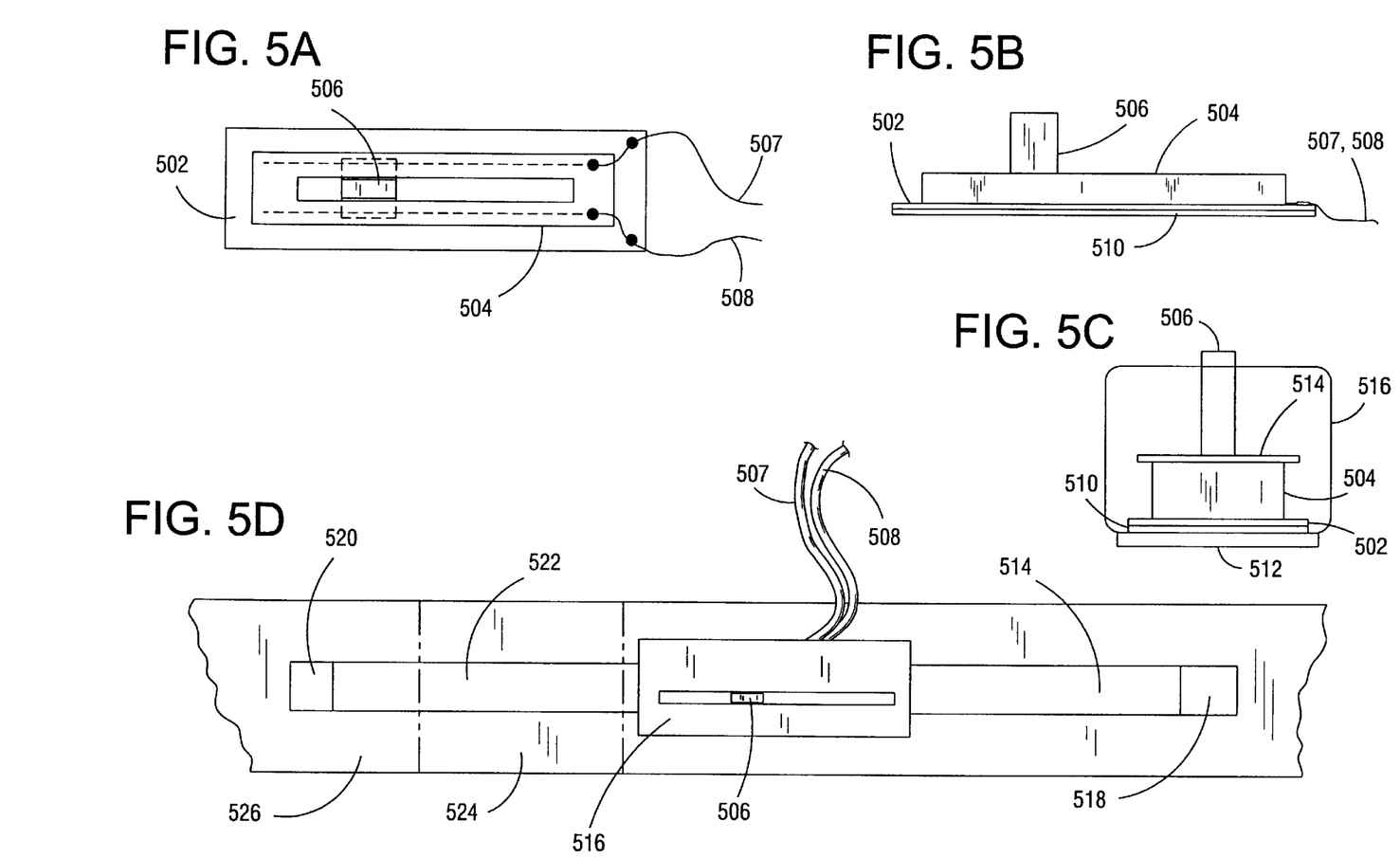
FIGS. 5A–5D illustrate a breathing sensor unit of the system of FIG. 1.

Referring next to FIG. 5A, a top view of the breathing sensor unit 104 without a belt 526 (see FIG. 5D) is shown. A linear slide potentiometer 504, or other variable resistor transducer is attached to the top of a breathing sensor circuit board 502. A slide knob 506 extends through the top of the linear slide potentiometer 504. A power supply wire 507 provides a positive five volt potential to the breathing sensor circuit board 502. A sensor output wire 508 from the breathing sensor circuit board 502 connects to the integration unit 108 and carries the breathing signal for the breathing sensor unit. In one preferred embodiment, the power supply wire 507 originates from the signal processing unit 110.

Referring next to FIG. 5B, a lateral view of the breathing sensor unit 104, also without the belt 526, is shown. The slide knob 506 is shown extending from the top of the linear slide potentiometer 504. The linear slide potentiometer 504 outputs differing resistances as the slide knob 506 moves back and forth along a long axis of the linear slide potentiometer 504. A breathing sensor circuit board attachment means 510 such as Velcro, clips, or snaps is affixed to the underside of the breathing sensor circuit board 502.

Referring next to FIG. 5C, an end view of the breathing sensor unit 104 without the belt 526 is shown. The slide knob 506 extends through a sensor case 516, which houses the linear slide potentiometer 504 and the breathing sensor circuit board 502. The breathing sensor circuit board attachment means 510 affixes the breathing sensor circuit board 502 to the inside bottom of the sensor case 516. A sensor case attachment means 512 affixes the sensor case 516 to the belt 526. An elastic lead 514 is fixedly attached to the slide knob 506 to move the slide knob 506 as tension on the elastic lead 514 is applied.

Referring next to FIG. 5D, a detailed, partial top view of the breathing sensor unit 104 attached to the belt 526 is shown. The sensor case 516 containing the slide knob 506, linear slide potentiometer 504, and the breathing sensor circuit board 502 is removably attached to the belt 526 via the sensor case attachment means 512. The power supply wire 507 provides a positive five volt potential to the breathing sensor circuit board 502. The sensor output wire 508 from the breathing sensor circuit board 502 connects to the integration unit 108 and carries the breathing signal for the breathing sensor unit. An attachment lead 522, fixedly attached to one end of the sensor case 516, extends from the sensor case 516 to a first tab 520 on the belt 526. The elastic lead 514, attached to the slide knob 506, extends from the other end of the sensor case 516 and attaches to a second tab 518 on the belt 526. In one embodiment, the first and second tabs 518, 520 are Velcro tabs and the attachment lead 522 is a strip of Velcro. A portion of the belt 526 underneath the attachment lead 522 is composed of an elastic material 524. The elastic material 524 allows the belt 526 to expand and contract while maintaining closeness between the belt 526 and the user's torso. The attachment lead 522 anchors the sensor case 516 to the belt 526 while the elastic lead 514 allows the slide knob 506 to move as the belt 526 expands and contracts. The belt 526 is adjustable to fit many torso sizes from young children to adults.

Once the belt 526 is positioned adjacent to the user's torso, the belt 526 expands and contracts as the user 102 inhales and exhales respectively. Because the first and second tabs 518, 520 are fixedly attached to the belt 526 and the attachment lead 522 is non-elastic, the elastic lead 514 expands and contracts with the belt 526 drawing the slide knob 506 back and forth. As the slide knob 506 moves, the linear slide potentiometer 504 outputs various resistances corresponding to the location of the slide knob 506 at a given time.

In an alternative embodiment, the signal processing unit 110 is a laptop computer with two joystick inputs as the analog input 112. With two joystick inputs, the breathing measurement circuitry 400 in the integration unit 108 is no longer necessary. The abdominal and thoracic breathing signals are transmitted directly to the laptop computer as separate breathing signals at line 124. Similarly, the software associated with the processor 114 in the laptop is correspondingly simplified to accommodate the two separate breathing signals at line 124.

In another alternative embodiment, the comparison between the output of voicing detection lowpass filter 308 and the output from volume lowpass filter 212, previously carried out by voicing detection comparator 312, occurs within the software associated with processor 114. If signal processing unit 110 is a laptop computer with a first and a second joystick inputs, then voltage divider 310 and voicing detection comparator 312 are eliminated from integration unit 108 in this embodiment. The output from voicing detection lowpass filter 308 connects to a voicing detection voltage-to-current converter (not shown) and then to the X input of the second joystick input. The output from the voltage-to-current converter 214 connects to the Y input of the second joystick input. The signals from breathing sensor units 104 pass directly to the X and Y inputs of the first joystick input.

Referring next to FIG. 6, a graph illustrates a vocal tract sound signal representation 604 superimposed onto an integrated breathing signal representation 606. The graph is produced by the software associated with the processor 114. In one embodiment, the software runs on the laptop computer with Windows 95 or higher as an operating system. In this embodiment, the software is user-friendly and portable from one location to another. The vertical axis indicates a volume of air in the user's lungs as measured by the breathing sensor units 104, and the horizontal axis represents time. The integrated breathing signal representation 606, representing the volume of air, is shown as a line increasing and decreasing along the vertical axis as the user 102 inhales and exhales over time, respectively. During the respiratory cycle, the user 102 may emit the vocal tract sounds 122. The intensity of the vocal tract sounds 122 is shown as the vocal tract sound signal representation 604 in FIG. 6. The vocal tract sound signal representation 604 is superimposed onto the integrated breathing signal representation 606, and is shown as a vertical thickening of the line indicating the integrated breathing signal representation 606, with a thickness proportional to the intensity of the vocal tract sounds 122. Using an integrated pneumotachographic signal for comparison (as the clinical standard), the preferred embodiment of the invention has been shown to collect valid data about volume-related breathing behavior.

The integrated breathing signal representation 606 illustrates either the abdominal breathing signal, the thoracic breathing signal, or a composite signal which is the sum of the abdominal and thoracic breathing signals. The composite signal (see FIG. 7) indicates relative volume and volumetric displacement. FIG. 6 indicates either the abdominal or thoracic breathing signal. The software also allows the user 102 to view a split-screen display with a first screen indicating the abdominal breathing signal and a second screen indicating the thoracic breathing signal.

In one embodiment, the output from the voicing detection circuitry 300 indicates the presence or absence of voicing. The line indicating the integrated breathing signal 128 has a thickness representative of the intensity of any sound transduced by the microphone 106 (including speech, background noise, etc.). When the presence of voicing is detected via a fundamental frequency, the thickness of the line indicating the integrated breathing signal 128 is colored red to indicate phonation. When the absence of voicing is detected, the thickness of the line indicating the integrated breathing signal 128 is colored green. The presence of voicing after exhalation begins indicates voice onset 602. A determination of voice onset 602 notifies the user 102 that speech is detected, whether or not the user 102 intended to speak. Such a notification aids in the treatment of users 102 who are deaf or users 102 who stutter.

The vocal tract sound signal 126 may also indicate the presence of sound that is unrelated to user 102 such as background noise. In another embodiment, a separate comparator using a cut-off value differentiates speech-related sound from background noise. In this embodiment, the thickness of the line representing the integrated breathing signal 128 is colored black to indicate non-speech background noise.

Referring next to FIG. 7, a graph illustrates the vocal tract sound signal representation 604 superimposed on the integrated breathing signal representation 606 with recommended maximum 702 and minimum 704 breathing levels shown. FIG. 7 is similar to FIG. 6 except that the integrated breathing signal representation 606 is the composite signal representing the sum of the abdominal and thoracic breathing signals. FIG. 7 also contains horizontal lines indicating the recommended maximum 702 and minimum 704 breathing levels of air volume for the user 102. In one embodiment, the lines representing the maximum 702 and minimum 704 levels are colored blue and enclose an area shaded in light blue in which the integrated breathing signal representation 606 should remain during the respiratory cycle.

The instructor or the user 102 determines the position of the maximum 702 and minimum 704 levels prior to treatment sessions by calibration. Initially, the tidal volume of user 102 is measured using the present invention to determine the approximate volume user 102 displaces simply for oxygen needs. The measurement represents the minimum level 704 of breathing volume. The instructor or user 102 inputs this measurement into signal processing unit 110. In a preferred embodiment where signal processing unit 110 is a laptop computer, the instructor or user 102 uses a mouse or keyboard of the laptop computer to input the minimum level 704 and display a representative horizontal line. The maximum level 702 of breathing volume is usually 1.5 times the minimum level 704. The maximum level 702 can be computed and displayed automatically with adjustment available to the instructor or user 102. It is the task of user 102 to stay within these suggested levels for optimal speech breathing volumes during speech production.

The vocal tract sound signal representation 604 superimposed onto the integrated breathing signal representation 606 illustrates a combined signal representation. In one embodiment, the combined signal representation is recorded for an interval of time. This recorded signal can be displayed later for the user 102. The software allows the instructor or the user 102 to begin recording, load a previous recording, close a current recording, save a current recording with a default file name, or save a current recording with a user-selected file name. In addition, the combined signal representation for the user 102 is displayed adjacent to or superimposed on the previous recording for instructional purposes. Alternatively, the instructor creates a recommended combined signal representation as a model for the user 102. The recommended combined signal representation represents the proper coordination of speech and breathing. This functionality is useful for teaching phrases of language. For example, to instruct the user 102 to properly associate speech with breathing, the user 102 produces the combined signal representation while viewing the previous recording or recommended combined signal representation illustrative of properly associated speech and breathing for a specific passage of text. In this manner, the user 102 can learn to imitate the speech and breathing production of the previous recording or the recommended combined signal representation.

In another embodiment, the system 100 of the invention further comprises a printer for producing a hard-copy of the combined signals on display 116 as viewed by the user 102. Alternately, a hard-copy of the combined signal representation is produced in real-time similar to the strip charts of an electrocardiograph. In this fashion, an instructor can maintain accurate records of the user's progress with the system 100.

In yet another embodiment, the software provides an animated character for use with children or those adults who cannot quickly interpret graphical displays. In this embodiment, a human representation on the display 116 visualizes abdominal and thoracic behaviors of the user 102 as measured by the breathing sensor units 104. The chest and abdomen of the human representation enlarge and shrink as the user 102 inhales and exhales, respectively. The vocal tract sound signal representation 604 is shown as an arrow extending from the human representation's mouth. The length of the arrow is proportional to the intensity of the vocal tract sounds 122. The color of the arrow indicates the presence (red) or absence (green) of voicing as detected by voicing detection circuitry 300.

In operation, the system 100 of the invention assesses vocal tract sound production and breathing of the user 102. The microphone 106 produces the vocal tract sound signal 126 by transducing the vocal tract sounds of user 102. The breathing signal 124 represents the breathing movement 120 of the user 102. The analog input 112 receives the vocal tract sound 126 and breathing 124 signals for processing. The vocal tract sound 126 and breathing 124 signals are combined by superimposition for display to the user 102. The system 100 is useful in training speech to the deaf, treating persons who stutter, or speakers whose speech is impaired by brain lesions.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A system for assessing breathing and vocal tract sound production of a user comprising:
    a first sensor generating a vocal tract sound signal representing vocal tract sounds produced by the user;
    a second sensor generating a breathing signal representing breathing movement of the user, said second sensor comprising a first breathing sensor positioned adjacent to an abdominal area of the user for producing an abdominal breathing signal, said second sensor further comprising a second breathing sensor positioned adjacent to a thoracic area of the user for producing a thoracic breathing signal;
    an integration unit receiving the abdominal and thoracic breathing signals and selectively outputting either the abdominal or the thoracic breathing signal as the breathing signal; and
    a signal processing unit for processing the vocal tract sound and breathing signals, said signal processing unit including an analog input receiving the vocal tract sound and breathing signals from the first and second sensors, respectively, and a processor generating a combined signal representing a superimposition of the received signals to the user.

2. The system of claim 1, wherein the first sensor comprises a microphone connected to the analog input, said microphone receiving the vocal tract sounds produced by the user, producing the vocal tract sound signal, and transmitting the vocal tract sound signal to the signal processing unit via the analog input.

3. The system of claim 1, wherein the second sensor comprises at least one breathing sensor connected to the analog input, said breathing sensor receiving the breathing movement of the user, producing the breathing signal, and transmitting the breathing signal to the signal processing unit via the analog input.

4. The system of claim 1, wherein the integration unit produces a breathing source signal indicating which of the abdominal and thoracic breathing signals is being output as the breathing signal.

5. The system of claim 1, wherein the integration unit alternates between outputting the abdominal and thoracic breathing signals as the breathing signal as a function of a user-defined sampling rate.

6. A system for assessing breathing and vocal tract sound production of a user comprising:
    a first sensor generating a vocal tract sound signal representing vocal tract sounds produced by the user;
    a second sensor generating a breathing signal representing breathing movement of the user;
    a signal processing unit for processing the vocal tract sound and breathing signals, said signal processing unit including an analog input receiving the vocal tract sound and breathing signals from the first and second sensors, respectively, and a processor generating a combined signal representing a superimposition of the received signals to the user; and
    a voicing detection circuit for identifying portions of the vocal tract sound signal as being voiced speech sounds.

7. The system of claim 1, further comprising a volume circuit for amplifying the vocal tract sound signal.

8. A system for assessing breathing and vocal tract sound production of a user comprising:
   a first sensor generating a vocal tract sound signal representing vocal tract sounds produced by the user;
   a second sensor generating a breathing signal representing breathing movement of the user; and
   a signal processing unit for processing the vocal tract sound and breathing signals, said signal processing unit including an analog input receiving the vocal tract sound and breathing signals from the first and second sensors, respectively, and a processor generating a combined signal representing a superimposition of the received signals to the user, wherein the signal processing unit comprises a personal computer and wherein the analog input comprises at least one joystick input of the personal computer.

9. A system for assessing breathing and vocal tract sound production of a user comprising:
   a first sensor generating a vocal tract sound signal representing vocal tract sounds produced by the user;
   a second sensor generating a breathing signal representing breathing movement of the user; and
   a signal processing unit for processing the vocal tract sound and breathing signals, said signal processing unit including an analog input receiving the vocal tract sound and breathing signals from the first and second sensors, respectively, and a processor generating a combined signal representing a superimposition of the received signals to the user, wherein the processor defines minimum and maximum breathing volume levels as a function of user input and further comprising a display for displaying the combined signal in conjunction with the minimum and maximum breathing volume levels to the user.

10. The system of claim 1, further comprising a printer for producing a hard-copy representation of the combined signal in approximately real-time.

11. The system of claim 1, further comprising a printing device for producing a hard-copy representation of the combined signal for a preset interval of time.

12. The system of claim 1, further comprising software operative with the processor for superimposing the received vocal tract sound and breathing signals.

13. A system for assessing breathing and vocal tract sound production of a user comprising:
   a first sensor generating a vocal tract sound signal representing vocal tract sounds produced by the user;
   a second sensor generating a breathing signal representing breathing movement of the user, wherein the second sensor comprises at least one breathing sensor measuring volumetric displacement indicating the breathing movement of the user, said breathing sensor comprising:
      at least one belt positioned around a torso area of the user; and
      a variable resistor transducer attached to the belt, said transducer outputting the breathing signal as a function of differing resistances caused by expansion and contraction of the belt due to the breathing movement of the user; and
   a signal processing unit for processing the vocal tract sound and breathing signals, said signal processing unit including an analog input receiving the vocal tract sound and breathing signals from the first and second sensors, respectively, and a processor generating a combined signal representing a superimposition of the received signals to the user.

14. The system of claim 13 wherein the belt comprises:
   an attachment lead connected to the transducer;
   a first tab for connecting the attachment lead to the belt;
   an elastic lead connected to a slide knob of the transducer, wherein moving said slide knob within a limited range of motion causes the resistance output of the transducer to vary proportionately; and
   a second tab for connecting the elastic lead to the belt.

15. The system of claim 14 wherein the belt further comprises elastic material for allowing expansion and contraction of the belt which similarly expands and contracts the elastic lead, wherein the elastic lead moves the slide knob within the limited range of motion to proportionately output varying resistances from the transducer.

16. A system for assessing speech sound production and breathing of a user comprising:
   a first sensor generating a speech sound signal representing speech sounds produced by the user;
   a second sensor generating a breathing signal representing breathing movement of the user, said second sensor comprising a first breathing sensor positioned adjacent to an abdominal area of the user for producing an abdominal breathing signal, said second sensor further comprising a second breathing sensor positioned adjacent to a thoracic area of the user for producing a thoracic breathing signal;
   an integration unit receiving the abdominal and thoracic breathing signals and selectively outputting either the abdominal or the thoracic breathing signal as the breathing signal; and
   a signal processing unit for processing the speech sound and breathing signals, said signal processing unit including an analog input receiving the speech sound and breathing signals from the first and second sensors, respectively, and a processor generating a combined signal representing a superimposition of the received signals to the user.

17. A method for assessing breathing and vocal tract sound production of a user comprising the steps of:
   sensing vocal tract sounds produced by the user and providing a vocal tract sound signal representative thereof;
   sensing breathing movement of the user and providing abdominal and thoracic breathing signals representative thereof via an integration unit, said integration unit selectively outputting either the abdominal or the thoracic breathing signal;
   receiving the signals via an analog input for processing the signals;
   generating a combined signal by superimposing the vocal tract sound and breathing signals; and
   displaying the combined signal to the user.

18. The method of claim 17, wherein the step of generating occurs in software.

19. The method of claim 17, further comprising the step of recording the superimposition of signals for an interval of time.

20. The method of claim 19, further comprising the step of displaying the recorded superimposition of signals to the user while displaying the current superimposition of signals of the user in approximately real-time.

21. The method of claim 17, further comprising the step of displaying a recommended superimposition of signals to the user while displaying the current superimposition of signals of the user in approximately real-time.

* * * * *